(12) United States Patent
Vogt et al.

(10) Patent No.: US 9,309,205 B2
(45) Date of Patent: Apr. 12, 2016

(54) FILTRATION PROCESS FOR PURIFYING LIQUID AZOLE HETEROAROMATIC COMPOUND-CONTAINING MIXTURES

(71) Applicant: Wincom, Inc., Blue Ash, OH (US)

(72) Inventors: Peter F. Vogt, Loveland, OH (US); James E. Milawski, Maineville, OH (US); Michael E. Lees, Cincinnati, OH (US); Alexander J. Wessel, Erlanger, KY (US)

(73) Assignee: Wincom, Inc., Blue Ash, OH (US)

( * ) Notice: Subject to any disclaimer, the term of this patent is extended or adjusted under 35 U.S.C. 154(b) by 0 days.

(21) Appl. No.: 14/064,465

(22) Filed: Oct. 28, 2013

(65) Prior Publication Data

US 2015/0119578 A1    Apr. 30, 2015

(51) Int. Cl.
C07D 249/16    (2006.01)
C07D 249/18    (2006.01)

(52) U.S. Cl.
CPC .................................. C07D 249/18 (2013.01)

(58) Field of Classification Search
USPC ........................................................ 548/257
See application file for complete search history.

(56) References Cited

U.S. PATENT DOCUMENTS

| | | |
|---|---|---|
| 3,537,999 A | 11/1970 | Kennedy |
| 3,559,786 A | 2/1971 | Long |
| 3,597,353 A | 8/1971 | Randell et al. |
| 3,732,239 A | 5/1973 | Spatz et al. |
| 3,833,502 A | 9/1974 | Leary et al. |
| 3,849,433 A | 11/1974 | Butula et al. |
| 3,970,667 A | 7/1976 | Gengnagel et al. |
| 4,060,491 A | 11/1977 | Bridger et al. |
| 4,066,823 A | 1/1978 | Armstrong |
| 4,144,188 A | 3/1979 | Sato |
| 4,315,889 A | 2/1982 | McChesney et al. |
| 4,406,811 A | 9/1983 | Christensen et al. |
| 4,436,523 A | 3/1984 | Hugelshofer et al. |
| 4,675,158 A | 6/1987 | Kindera |
| 4,701,273 A | 10/1987 | Brady et al. |
| 4,734,209 A | 3/1988 | Phillips et al. |
| 4,735,717 A | 4/1988 | Sims |
| 4,744,950 A | 5/1988 | Hollander |
| 4,865,744 A | 9/1989 | Hartling et al. |
| 4,898,687 A | 2/1990 | Parker et al. |
| 4,918,195 A | 4/1990 | Schnegg et al. |
| 4,959,161 A | 9/1990 | Clubley |
| 4,976,919 A | 12/1990 | Skold et al. |
| 5,013,482 A | 5/1991 | O'Neil |
| 5,055,230 A | 10/1991 | Clubley et al. |
| 5,091,113 A | 2/1992 | Clubley |
| 5,096,584 A | 3/1992 | Reddy et al. |
| 5,411,668 A | 5/1995 | Pollmann et al. |
| 5,538,642 A | 7/1996 | Solie |
| 5,681,467 A | 10/1997 | Solie et al. |
| 5,914,409 A * | 6/1999 | Adkins ................ C07D 249/18 548/257 |
| 5,932,105 A | 8/1999 | Kelly |
| 5,958,849 A | 9/1999 | Hewson et al. |
| 6,001,838 A | 12/1999 | Stockhammer et al. |
| 6,074,992 A | 6/2000 | Levesque |
| 6,448,207 B1 | 9/2002 | Fukutani et al. |
| 6,448,749 B2 | 9/2002 | Pochmuller |
| 6,551,552 B1 | 4/2003 | Lyublinski et al. |
| 6,585,933 B1 | 7/2003 | Ehrhardt et al. |
| 6,616,847 B1 | 9/2003 | Teipel et al. |
| 6,706,670 B2 | 3/2004 | Kalota et al. |
| 6,716,281 B2 | 4/2004 | Bernards et al. |
| 6,881,336 B2 | 4/2005 | Johnson |
| 6,946,027 B2 | 9/2005 | Bernards et al. |
| 6,984,340 B1 | 1/2006 | Brady et al. |
| 7,108,795 B2 | 9/2006 | Bernards et al. |
| 7,186,354 B2 | 3/2007 | Aoki et al. |
| 7,291,581 B2 | 11/2007 | Levine et al. |
| 7,393,395 B2 | 7/2008 | Aiba et al. |
| 7,575,687 B2 | 8/2009 | Kurth et al. |
| 8,070,088 B2 | 12/2011 | Tortosa |
| 8,101,074 B2 | 1/2012 | Larsen |
| 8,182,694 B2 | 5/2012 | Childs et al. |
| 8,236,177 B1 | 8/2012 | Wood |

(Continued)

FOREIGN PATENT DOCUMENTS

| | | |
|---|---|---|
| DE | 1948794 | 4/1971 |
| GB | 1331606 | 9/1973 |

(Continued)

OTHER PUBLICATIONS

Cobratec 911S Specification (Mar. 23, 1999).

(Continued)

*Primary Examiner* — Nyeemah A Grazier
*Assistant Examiner* — Sagar Patel
(74) *Attorney, Agent, or Firm* — Eric W. Guttag; Eric W. Guttag IP Law Office (57) ABSTRACT

A process for removing impurities from a liquid azole heteroaromatic compound-containing (e.g., triazole-containing) mixture by: (a) providing a liquid azole heteroaromatic compound-containing mixture having impurities; and (b) passing the azole heteroaromatic compound-containing mixture through at least one filtration membrane which is a nanofiltration membrane and/or ultrafiltration membrane having a molecular pore size in the range of from about 200 daltons to about 1 kilodaltons to provide a permeate that is an at least partially purified azole heteroaromatic compound-containing mixture and a retentate with at least some impurities.

16 Claims, 5 Drawing Sheets

(56) References Cited

U.S. PATENT DOCUMENTS

| | | |
|---|---|---|
| 8,236,204 B1 | 8/2012 | Matulewicz et al. |
| 8,236,205 B1 | 8/2012 | Matulewicz et al. |
| 8,348,499 B2 | 1/2013 | Jons et al. |
| 8,535,567 B2 | 9/2013 | Matulewicz et al. |
| 8,535,568 B2 | 9/2013 | Matulewicz et al. |
| 8,535,569 B2 | 9/2013 | Matulewicz et al. |
| 2001/0030315 A1 | 10/2001 | Aoki et al. |
| 2002/0043501 A1 | 4/2002 | Irvine |
| 2002/0153309 A1 | 10/2002 | Irvine |
| 2003/0063998 A1 | 4/2003 | Ghosh et al. |
| 2003/0063999 A1 | 4/2003 | Ghosh et al. |
| 2003/0065116 A1 | 4/2003 | Ghosh et al. |
| 2004/0127633 A1* | 7/2004 | Guth .............. C08G 73/18 524/548 |
| 2004/0235681 A1 | 11/2004 | Levine et al. |
| 2005/0020457 A1 | 1/2005 | Rohrbach et al. |
| 2005/0069997 A1* | 3/2005 | Adkesson .............. B01D 1/027 435/158 |
| 2005/0199551 A1 | 9/2005 | Gordon |
| 2005/0238811 A1 | 10/2005 | Bernards et al. |
| 2006/0019840 A1 | 1/2006 | Kawahara et al. |
| 2007/0102361 A1 | 5/2007 | Kiefer et al. |
| 2007/0114177 A1 | 5/2007 | Sabottke |
| 2007/0184114 A1 | 8/2007 | Cevc |
| 2007/0191240 A1 | 8/2007 | Suda |
| 2008/0035573 A1 | 2/2008 | Peiffer et al. |
| 2008/0067071 A1 | 3/2008 | Haas et al. |
| 2009/0281017 A1 | 11/2009 | Suzuki et al. |
| 2010/0022424 A1 | 1/2010 | Vogt et al. |
| 2010/0022425 A1 | 1/2010 | Michel et al. |
| 2010/0137174 A1 | 6/2010 | Maeda et al. |
| 2010/0213128 A1 | 8/2010 | Bradford et al. |
| 2011/0100914 A1 | 5/2011 | Mairal et al. |

FOREIGN PATENT DOCUMENTS

| | | |
|---|---|---|
| GB | 1518342 | 7/1974 |
| GB | 1581407 | 12/1980 |
| WO | WO 94/09888 | 5/1994 |
| WO | WO 0066810 | 11/2000 |
| WO | WO 02102945 | 12/2002 |
| WO | WO 03004476 | 1/2003 |
| WO | WO 03044140 | 5/2003 |
| WO | WO 2005/081627 | 9/2005 |
| WO | WO 2006029966 | 3/2006 |
| WO | WO 2006053858 | 5/2006 |
| WO | WO 2007135017 | 11/2007 |
| WO | WO 2008015116 | 2/2008 |
| WO | WO 2008055797 | 5/2008 |
| WO | WO 2009134716 | 11/2009 |
| WO | WO 2010008694 | 1/2010 |

OTHER PUBLICATIONS

Cobratec 928 Specification, Multi-Metal corrosion Inhibitor, pp. 1-2 (Sep. 9, 1998).

Cobratec Corrosion Inhibitors, Cobratec 928 Specification, Multi-Metal corrosion Inhibitor, pp. 1-2 (Sep. 13, 1995).

Wintrol HT90 (90%) Tetrahydro tolyltriazole, Determination of General Physico-Chemical Properties, pp. 1-32 (Apr. 26, 2000).

Wells, "Commercial Triazoles and Their Properties," AWT Meeting in Palm Springs, Sep. 21-24, 2005, AWT Journal of Spring 2007, vol. 14, No. 2, pp. 24-35.

International Search Report and Written Opinion of the International Search Authority (mailed Jan. 9, 2015) for PCT/US14/61885, 11 pages.

* cited by examiner

FILTRATION PROCESS FOR PURIFYING LIQUID AZOLE HETEROAROMATIC COMPOUND-CONTAINING MIXTURES

FIELD OF THE INVENTION

The present invention generally relates to a filtration process for purifying liquid azole heteroaromatic compound-containing (e.g., triazole-containing) mixtures by using a filtration membrane selected from nanofiltration and ultrafiltration membranes.

BACKGROUND

Triazoles, such as benzotriazoles, tolyltriazoles, etc., are known to be useful as corrosion inhibitors, including for metal or metal alloy surfaces, synthetic detergents and antifreezes, as UV stabilizers, as intermediates in numerous syntheses such as, for example, dyes, and in water treatment applications. See, for example, U.S. Pat. Appln. No. 20010022424 (Vogt et al), published Jan. 28, 2010 (use of triazoles to reduce cobalt leaching); U.S. Pat. No. 8,236,204 (Matulewicz et al.), issued Aug. 7, 2012 (corrosion inhibiting composition comprising aliphatic-substituted tetrahydrobenzotriazoles solubilized in tetrahydrobenzotriazole activating solvents); and U.S. Pat. No. 8,236,205 (Matulewicz et al.), issued Aug. 7, 2012 (corrosion inhibiting composition comprising tetrahydrobenzotriazoles and/or other triazoles such as benzotriazoles and/or tolyltriazoles). For these triazoles to be suitable for certain applications and uses, it may be necessary for these triazoles to have a relatively high degree of purity. For example, discoloration may occur during the manufacture of these triazoles due to chemical oxidation of compounds, such as, for example, ortho-diaminotoluene, in making tolyltriazoles. Accordingly, it may be necessary to purify these triazoles, such as tolyltriazoles, prior to use as corrosion inhibitors, etc.

Suitable processes for purifying triazoles, such as tolyltriazoles and benzotriazoles, are known and described, collectively, for example, in U.S. Pat. No. 5,914,409 (Adkins et al.), issued Jun. 22, 1999. For example, when crude ortho-diaminotoluene is used as the reactant before starting diazotization and ring closure reaction in making tolyltriazoles, it may be necessary to purify the resulting tolyltriazoles. One method for purifying the resulting tolyltriazoles is by extracting the reaction mixture containing the tolyltriazoles with chloroform, washing the resulting chloroform solution, distilling off the chloroform, and then recrystallizing the crude tolyltriazole from benzene to obtain purified tolyltriazole. See U.S. Pat. No. 3,732,239 (Spatz et al.), issued May 8, 1973. Alternatively, the reaction mixture containing the triazole (with no intermediate isolation of the tolyltriazole prepared by diazotization and ring closure reaction) may be made alkaline by using aqueous sodium hydroxide solution, may be subjected to several clarifying filtrations, and may then be acidified (e.g., by using nitric acid) to a pH of from about 4.5 to 6 to cause precipitation and isolation of the purified tolyltriazole. See U.S. Pat. No. 3,970,667 (Gengnagel et al.), issued Jul. 20, 1976. See also GB Patent Specification 1,581,407 published Dec. 10, 1980, which discloses distilling off volatile components from the reaction mixture, and then recovering the triazole (e.g., benzotriazole) from the distilled mixture by crystallization.

SUMMARY

According to a first broad aspect of the present invention, there is provided a process for removing impurities from a liquid azole heteroaromatic compound-containing mixture, which comprises the following steps:
- (a) providing a liquid azole heteroaromatic compound-containing-mixture comprising impurities; and
- (b) passing the azole heteroaromatic-containing mixture of step (a) in a cross-flow manner through at least one filtration membrane selected from the group consisting of nanofiltration and ultrafiltration membranes and having a molecular pore size in the range of from about 200 daltons to about 1 kilodalton to provide a permeate comprising an at least partially purified azole heteroaromatic compound-containing mixture and a retentate comprising at least some impurities.

According to a second broad aspect of the present invention, there is provided a process for removing impurities from a liquid azole heteroaromatic compound-containing mixture, which comprises the following steps:
- (a) providing a liquid feed flow comprising an azole heteroaromatic compound-containing mixture and having impurities;
- (b) providing a filtration system comprising: (1) an initial filtration section comprising at least one filtration unit; and (2) a final filtration section comprising at least one unit positioned after the initial filtration section, wherein each filtration unit of the initial filtration section, and the final filtration sections comprises one or more filtration membranes selected from the group consisting of nanofiltration membranes and ultrafiltration membranes, each filtration membrane having a molecular pore size in the range of from about 200 daltons to about 1 kilodaltons;
- (c) passing a first portion of the feed flow of step (a) in a cross-flow manner through each filtration unit of the initial filtration section of step (b) to provide an initial permeate comprising an at least partially purified azole heteroaromatic compound-containing mixture and an initial retentate comprising at least some impurities;
- (d) passing a second portion of the feed flow of step (a) in a cross-flow manner through each filtration unit of the final filtration section of step (b) to provide a final permeate comprising an at least partially purified azole heteroaromatic compound-containing mixture and a final retentate comprising at least some impurities; and
- (e) adding at least some of the initial and final retentates from steps (c) and (d) to the feed flow of step (a).

According to a third broad aspect of the present invention, there is provided a process for removing impurities from a liquid azole heteroaromatic compound-containing mixture, which comprises the following steps:
- (a) providing a liquid feed flow comprising an azole heteroaromatic compound-containing mixture and having impurities;
- (b) providing a filtration system comprising: (1) an initial filtration section comprising at least two parallel filtration units; (2) an intermediate filtration section positioned after the initial filtration section having one or more intermediate filtration subsections, each intermediate filtration subsection comprising at least two parallel filtration units; and (3) a final filtration section comprising at least two parallel filtration units positioned after the intermediate filtration section, wherein each filtration unit of the initial filtration section, each intermediate filtration subsection and the final filtration section each comprise one or more filtration membranes selected from the group consisting of nanofiltration membranes and ultrafiltration membranes, each filtration membrane having a molecular pore size in the range of from about 200 daltons to about 1 kilodalton;

(c) passing a first portion of the feed flow of step (a) in a cross-flow manner through each filtration unit of the initial filtration section of step (b) to provide an initial permeate comprising an at least partially purified azole heteroaromatic compound-containing mixture and an initial retentate comprising at least some impurities;

(d) passing a second portion of the feed flow of step (a) in a cross-flow manner through each filtration unit of each intermediate filtration subsection of the intermediate filtration section of step (b) to provide an intermediate permeate comprising an at least partially purified azole heteroaromatic compound-containing mixture and an intermediate retentate comprising at least some impurities;

(e) passing a third portion of the feed flow of step (a) in a cross-flow manner through each filtration unit of the final filtration section of step (b) to provide a final permeate comprising an at least partially purified azole heteroaromatic compound-containing mixture and a final retentate comprising at least some impurities; and (f) adding at least some of the initial, intermediate, and final retentates from steps (c) through (e) to the feed flow of step (a).

BRIEF DESCRIPTION OF THE DRAWINGS

The invention will be described in conjunction with the accompanying drawing, in which.

DETAILED DESCRIPTION

It is advantageous to define several terms before describing the invention. It should be appreciated that the following definitions are used throughout this application.
Definitions Where the definition of terms departs from the commonly used meaning of the term, applicant intends to utilize the definitions provided below, unless specifically indicated.

For the purposes of the present invention, the term "comprising" means various compositions, compounds, ingredients, components, elements, capabilities and/or steps, etc., may be conjointly employed in the present invention. Accordingly, the term "comprising" encompasses the more restrictive terms "consisting essentially of" and "consisting of."

For the purposes of the present invention, the term "azole heteroaromatic compound" refers to the class of azole heterocylic aromatic compounds which may include triazoles, thiazoles (e.g., mercaptobenzothiazole (MBT)), oxazoles, imidazoles, as well as mixtures thereof.

For the purposes of the present invention, the term "triazoles" refers to one or more azole heteroaromatic compounds having the general formula I:

I wherein $R_1$ is one or more of: a hydrogen group (i.e., H), a hydroxy group, an aliphatic group, or an aromatic group, $R_2$ is H, or an aliphatic group; as well as salts of these compounds of formula II (e.g., sodium salts, potassium salts, ammonium salts, etc.). The one or more $R_3$ groups may be at one or more of the 4, 5, 6 and/or 7 positions on the benzene ring. In the some embodiments, $R_1$ may be one aliphatic group, with the remaining $R_1$ being a hydrogen group (i.e., H). These triazoles may include benzotriazole (referred to herein interchangeably as "BT"), tolyltriazole (referred to herein interchangeably as toluyltriazole, tolutriazole, or "TT") which may be 4-methyl-benzotriazole (referred to herein interchangeably as "4-MeBT"); 5-methyl-benzotriazole (referred to herein interchangeably as "5-MeBT"), or a mixture thereof; butyl-benzotriazole (referred to herein interchangeably as "BBT") which may be, for example, 4-butyl-benzotriazole, 5-butyl-benzotriazole, or a mixture thereof; pentoxy-benzotriazole (referred to herein interchangeably as "Pentoxy BT") which may be 4-pentoxy-benzotriazole (referred to herein interchangeably as "4-Pentoxy BT"), 5-pentoxy-benzotriazole (referred to herein interchangeably as "5-Pentoxy BT"), or a mixture thereof; carboxy-benzotriazole (referred to herein interchangeably as "Carboxy BT") which may be 4-carboxy-benzotriazole (referred to herein interchangeably as "4-Carboxy BT"), 5-carboxy-benzotriazole (referred to herein interchangeably as "5-Carboxy BT"), or a mixture thereof as either the acid(s) or a water-soluble salt(s) thereof (e.g., sodium salt, potassium salt, etc.); N-1-bis(2-ethylhexyl)-aminomethyl-tolyltriazole (e.g., sold by Ciba Specialty Chemicals under the trade name Irgamet 39®); N-1-bis(2,2'-ethanol)-aminomethyl-tolyltriazole (e.g., sold by Ciba Specialty Chemicals under the trade name Irgamet 42®); sodium, potassium, or ammonium salts of, for example, TT, BT, or BBT; etc. These triazoles may be unhydrogenated, partially hydrogenated, or completely hydrogenated.

For the purposes of the present invention, the term "tetrahydrobenzotriazoles" (referred to interchangeably herein as "tetrahydrogenated benzotriazoles" or "THBs") refers to one or more compounds having the general formulas IIa or IIb:

IIa or wherein $R_3$ is one or more of: a hydrogen group (i.e., H), a hydroxy group, or an aliphatic group; and wherein $R_4$ is a hydrogen group (i.e., H), or an aliphatic group; as well as salts of these compounds of formulas IIa or IIb. The aliphatic $R_3$ groups may be at one or more of the 4, 5, 6 and/or 7 positions on the cyclohexane ring. In the some embodiments, $R_3$ may be one aliphatic group, with the remaining $R_3$ being a hydrogen group (i.e., H). The salts of these tetrahydrobenzotriazoles may include, for example, the potassium salts, the ammonium salts, etc. These tetrahydrobenzotriazoles may include, for example, tetrahydrobenzotriazole (i.e., 4,5,6,7-tetrahydrobenzotriazole, also referred herein interchangeably as "THBT"), tetrahydrotolulytriazole (referred to herein interchangeably as tetrahydrotoluyltriazole or "THTT") which may be 4-methyl-1H-benzotriazole, 5-methyl-1H-benzotriazole, or a mixture thereof; sodium, potassium, or ammonium salts of THBT or THTT; etc., as well as blends, mixtures, etc., of these tetrahydrobenzotriazoles. See, for example, U.S. Pat. No. 3,597,353 (Randell et al.), issued Aug. 3, 1971; and U.S. Pat. No. 3,849,433 (Butula et al.), issued Nov. 19, 1974, the entire contents and disclosures of which are herein incorporated by reference, for how to prepare tetrahydrobenzotriazoles from the respective benzotriazoles by catalytic hydrogenation, and which may also provide residual unhydrogenated benzotriazoles as the other triazoles for embodiments of compositions of the present invention.

For the purposes of the present invention, the term "aliphatic" refers to a carbon-containing moiety other than an aromatic moiety. Aliphatic moieties may be straight chain, branched chain, cyclic (cycloaliphatic), or any combination thereof, may be substituted or unsubstituted, may include one or more heteroatoms (e.g., oxygen atoms, nitrogen atoms, sulfur atoms, etc.) in the carbon chain (i.e., may be heterocyclic), may be unsaturated (i.e., one, two or more double bonds) or saturated, etc, and may have any desired number of carbon atoms, e.g., from 1 to 30 carbon atoms, for example from 1 to 12 carbon atoms, such as from 1 to 7 carbon atoms, (e.g., from 1 to 4 carbon atoms), etc. Aliphatic moieties suitable herein may include, but are not limited to, substituted or unsubstituted alkyl, alkenyl, alkadienyl, alkynyl, cycloalkyl, cycloalkenyl, etc. Suitable aliphatic moieties may include, but are not limited to, straight or branched chain alkyl (e.g., methyl, ethyl, propyl, isopropyl, butyl, isobutyl, pentyl, hexyl, heptyl, etc.) and substituted alkyl (e.g., hydroxylmethyl, hydroxyethyl, trifluoromethyl, alkoxymethyl, etc.), alkoxy, substituted amino (e.g., dimethylamino, etc.), carboxy, ester, amide, sulfonamide, carbamate, acyl (i.e., aldehyde or keto), etc., or any combination thereof.

For the purposes of the present invention, the term "aromatic" refers to an unsaturated cyclic arene moiety containing one or more unsaturated cyclic rings (for example, 5 and/or 6 atoms per ring) that may be substituted, unsubstituted, or a combination thereof, may be heterocyclic (i.e., including one or more oxygen atoms, nitrogen atoms, sulfur atoms, etc.), nonheterocyclic, or a combination thereof, may have any desired number of carbon atoms, e.g., from 3 to 30 carbon atoms, for example, from 3 to 18 carbon atoms, e.g., from 3 to 12 carbon atoms, etc. Aromatic moieties suitable herein may include, but are not limited to, substituted or unsubstituted phenyl, naphthyl, biphenyl, binaphthyl, phenanthenryl, anthracenyl, pyridinyl, pyrimidinyl, purinyl, pyrinyl, furanyl, thiophenyl, benzofuranyl, benzothiophenyl, dibenzofuranyl, dibenzothiophenyl, imidazolyl, oxazolyl, thiazolyl, pyrazolinyl, indolyl, pyridazinyl, pyrazinyl, quinolinyl, isoquinolinyl, benzoquinolinyl, phenanthrolinyl (e.g., 1,10-phenanthrolyl), carbazolyl, etc. Suitable aromatic moieties may include, but are not limited to, aromatics substituted with straight or branched chain alkyl (e.g., methyl, ethyl, propyl, isopropyl, butyl, isobutyl, pentyl, hexyl, heptyl, etc.) and substituted alkyl (e.g., hydroxymethyl, hydroxyethyl, trifluoromethyl, alkoxymethyl, etc.), amino and substituted amino (e.g., dimethylamino, etc.), hydroxy (e.g., a phenolic), carboxy, sulfonate, ester, amide, sulfonamide, carbamate, acyl (i.e., aldehyde or ketone), nitro, etc., or any combination thereof.

For the purposes of the present invention, the term "azole heteroaromatic compound-containing mixture" refers to mixture comprising a measurable amount of one or more triazoles. For example, the triazoles may be present in this mixture in an amount of at least about 5%, such as at least about 40%, (e.g., at least about 50%). The azole heteroaromatic compound-containing mixture may be concentrated or unconcentrated (e.g., dilute), and may have a pH of, for example, at least about 9 (e.g., a pH in the range of from about 10 to about 14).

For the purposes of the present invention, the term "purified azole heteroaromatic compound-containing mixture" refers to a azole heteroaromatic compound-containing mixture from which at least a measurable quantity of impurities have been removed by filtration, e.g., at least as low as 500 ppm of impurities removed.

For the purposes of the present invention, the term "impurities" refers to components other than azole heteroaromatic compounds which may be present in an azole heteroaromatic compound-containing mixture. These impurities may comprise soluble and/or insoluble color-forming components such as aromatic polymers (e.g., Aniline Black and other amine condensation polymers, as well as colorless or opaque (e.g., may form a "haze") components which may be soluble when concentrated but insoluble when diluted such as nonfunctional macromolecules (e.g., polymers without ionizable functional groups). These impurities may be present measurable quantities in azole heteroaromatic compound-containing mixtures in amounts of up to about 10%, e.g., may be present in the range of from about 0.5 to about 8%).

For the purposes of the present invention, the term "color-forming components" refers to one or more components that are impurities and which impart a visible color which may appear as (light) yellowish, brownish, reddish, blackish, etc. The molecular weight of these color-forming components often determines what color those components appear as in the visible color spectra.

For the purposes of the present invention, the term "filtration" refers to a filtration process involving a cross-flow filtration technique wherein the liquid composition, mixture, solution, etc., is passed, under pressure, through one or more filtration membranes selected from the group consisting of nanofiltration membranes and ultrafiltration membranes. Pressures which may be used in embodiments of the filtration process of the present invention may be in the range of from about 1 to about 2500 psi, such as from about 100 to about 500 psi.

For the purposes of the present invention, the terms "nanofiltration membrane" (also referred to interchangeably as a "nanofilter") and "ultrafiltration membrane" (also referred to interchangeably as a "ultrafilter") refer to filters comprising a porous membrane structure having an nominal molecular pore size in the range of from about 200 daltons to about 1000 daltons (1 kilodalton), for example, from about 250 daltons to about 600 daltons such as from about 350 to about 500 daltons. The particular molecular pore size for the filtration membranes which are useful in embodiments of the filtration process of the present invention may depend upon the age of the filtration membrane, the pressures employed in passing the liquid feed flow through these membranes, etc. Nanofiltration membranes, as well as ultrafiltration membranes, useful in embodiments of the process of the present invention may have tubular membrane structures, spiral membrane (also referred to as spiral-wound membrane) structures, hollow fiber membrane structures, etc. See, for example, U.S. Pat. No. 8,236,177 (Wood), issued Aug. 7, 2012; U.S. Pat. No. 8,182,894 (Childs et al.), issued May 22, 2012; U.S. Pat. No. 8,101,074 (Larsen), issued Jan. 24, 2012; U.S. Pat. No. 8,070,088 (Tortosa), issued Dec. 6, 2011; U.S. Pat. No. 7,635,428 (Marui et al.), issued Dec. 22, 2009; U.S. Pat. No. 5,538,642 (Solie), issued Jul. 23, 1996; U.S. Pat. No. 5,096,584 (Reddy et al.), issued Mar. 17, 1992; and U.S. Pat. No. 4,735,717 (Sims), issued Apr. 5, 1988, the entire contents and disclosures of which are herein incorporated by reference, for illustrative nanofiltration membranes having spiral membrane, tubular membrane, and hollow fiber membrane structures. Suitable commercially available spiral membrane structures and tubular membrane structures for use in the embodiments of the process of the present invention may include Dow's FilmTec™ NF270 spiral membrane structures, Dow's FilmTec™ AFC30 tubular membrane structures, etc.

For the purposes of the present invention, the term "cross-flow filtration" (also called "tangential-flow filtration") refers to a type of filtration where the feed flow of the liquid composition, mixture, solution, etc., passes tangentially across (e.g., parallel to) the surface of the filtration membrane under a positive pressure. In cross-flow filtration carried out according to embodiments of the filtration process of the present invention, the feed flow may be enter along the outer surface of the filtration membrane such that the permeate passes inwardly through the porous membrane structure to the central or inner core portion of the membrane, or the feed flow may enter through the central or core portion of the filtration membrane such that the permeate passes outwardly through the porous membrane structure to the outer surface of the membrane.

For the purposes of the present invention, the term "feed flow" refers to the liquid composition, mixture, solution, etc., which enters the filtration membrane during cross-flow filtration and which provides a retentate and a permeate. The feed flow comprises at least the azole heteroaromatic compound-containing mixture, but may also comprise a liquid carrier for the azole heteroaromatic compound-containing mixture.

For the purposes of the present invention, the term "liquid carrier" refers to a component which may be used to form a flowable (i.e., liquid) composition comprising the azole heteroaromatic compound-containing mixture (including any impurities therein). Suitable liquid carriers may include one or more of: water (i.e., to form an aqueous composition), alcohols, such as methanol, ethanol, propanol, isopropanol, etc., diols such as ethylene glycol, propylene glycol, diethylene glycol, etc., as well mixtures of these liquid carriers.

For the purposes of the present invention, the term "retentate" in cross-flow filtration refers to that portion of the composition, mixture, solution, etc., of the feed flow which is retained by or exits the filtration membrane without passing through the porous membrane structure of the nanofiltration membrane. Normally, the retentate comprises the residual impurities from the azole heteroaromatic compound-containing mixture that is passed through the nanofiltration membrane.

For the purposes of the present invention, the term "permeate" (which may referred to interchangeably as the "filtrate") in cross-flow filtration refers to that portion of the composition, mixture, solution, etc., of the feed flow which flows or passes out through the porous membrane structure of the nanofiltration membrane. Normally, the permeate(s) comprises the at least partially purified azole heteroaromatic compound-containing mixture.

For the purposes of the present invention, the term "filtration unit" refers to a structure which comprises one or more filtration membranes, normally positioned within surrounding pressure vessel. Where the filtration unit comprises a plurality of filtration membranes, the filtration membranes may be connected in series (i.e., one end of a filtration membrane adjacent/connected to one end of another filtration membrane), the number of filtration membranes being connected in series depending upon the length of the filtration unit, as well as the length of each filtration membrane present in the filtration unit.

For the purposes of the present invention, the term "filtration section" refers to one filtration subsection or a plurality of filtration subsections, wherein each filtration subsection comprises one filtration unit or a plurality of parallel filtration units (e.g., a pair of filtration units operating in parallel). The filtration membranes present in each the filtration unit of each filtration section/subsection may be of the same type of filtration membrane (e.g., all spiral membrane structures or all tubular membrane structures) or may comprise varying types of filtration membranes (e.g., some are spiral membrane structures, some are tubular membrane structures).

For the purposes of the present invention, the term "in series" refers to a plurality of (i.e., at least two) filtration membranes, filtration units, filtration sections, etc., which are positioned (e.g., connected) in linear configuration or sequence for linear (connected) operation, e.g., a pair of filtration membranes positioned end-to end, a vertical (stacked) column of filtration units connected in series, etc. By contrast, the term "in parallel" refers to a plurality of (i.e., at least two) filtration membranes, filtration units, etc., which are positioned in a parallel configuration for parallel (unconnected) operation, e.g., a pair of filtration units positioned parallel to each other for parallel (unconnected) operation, etc. The number of filtration sections/subsections which may be connected in series in embodiments of the filtration process of the present invention may be at least, for example, in the range from two to fifteen (e.g., a column of from two to fifteen vertically stacked filtration units connected in series), such as from two to six (e.g., a column of from two to six vertically stacked filtration units connected in series).

For the purposes of the present invention, the term "corrosion inhibitor" refers to a material, substance, composition, compound, component, etc., which reduces, decreases, diminishes, lowers, minimizes, etc., the rate of corrosion (e.g., General Corrosion rate, Pitting Corrosion rate, etc.) of a metal or metal alloy.

For the purposes of the present invention, the term "corrosion inhibiting amount" refers to an amount of a material, substance, composition, compound, component, etc., which is effective to provide a measurable degree of reduction, diminution, drop, decrease, etc., in the rate of corrosion (e.g., General Corrosion) of metal or metal alloy.

For the purposes of the present invention, the term "General Corrosion" (also called "Uniform Corrosion") refers to corrosion which takes place uniformly over the surface of metal/metal alloy surfaces in the presence of a corrosive agent, thereby causing a uniform removal of metal/metal alloy from the surface and thus a general thinning of the component comprising the metal/metal alloy. General Corrosion should be contrasted with "localized corrosion" such as pitting corrosion, crevice corrosion, etc. General Corrosion rates are measure herein as described in the Measurement of General Corrosion Rates section described below.

For the purposes of the present invention, the formulas used in the specification, in the claims or in the drawings may represent a single compound, a mixture of compounds, etc., unless otherwise specified.

Description

Embodiments of the present invention relate to a process for purifying azole heteroaromatic compound-containing mixtures, and especially triazole-containing mixtures such as mixtures comprising tolyltriazole (TT), benzotriazole (BT), butyl-benzotriazole (BBT), and/or their salts (e.g., sodium salts). The azole heteroaromatic compound-containing mixtures are passed, under pressure, through one or more filtration units comprising one or more nanofiltration and/or ultrafiltration membranes. The filtration membranes used in the embodiments of the process of the present invention may be spiral membrane structures (e.g., Dow's FilmTec™ NF270 spiral membranes), tubular membrane structures (e.g., Dow's FilmTec™ AFC30 tubular membranes), or may be a combination of spiral membrane structures and tubular membrane structures. This filtration process may be used to remove soluble or insoluble color-forming, as well as certain other impurities that may cause, for example, when diluted an insoluble "haze" in these azole heteroaromatic compound-containing mixtures. The use of these filtration membranes in filtration units of embodiments of the process of the present invention provide for cross-flow filtration of these azole heteroaromatic compound-containing mixtures which avoids, for example, filter cake retentate from being washed away during the filtration process, thus potentially increasing operational time of the filtration membranes, as well as permitting a continuous filtration process for purifying these azole heteroaromatic compound-containing mixtures.

It has also been discovered that knowing the molecular size of the components in these azole heteroaromatic compound-containing mixtures permits the selection of filtration membranes of the appropriate molecular pore size to remove the soluble or insoluble color-forming components, as well as other insoluble (e.g., "haze-forming") components that comprise the non-triazole impurities in these azole heteroaromatic compound-containing mixtures without needing to use prior distillation techniques. In particular, the filtration membranes used in embodiments of the process of the present invention have a molecular pore size in the range of from about 200 daltons to about 1000 daltons (1 kilodaltons), for example, from about 250 daltons to about 600 daltons, such as from about 350 to about 500 daltons. In some embodiments, the desired purified azole heteroaromatic compound-containing mixtures, normally as one or more permeates, may be obtained which comprise components having a molecular weight below about 500 daltons, such as below about 300 daltons, e.g., the "higher end" cut off for desired components in the permeate may be somewhere in the molecular weight range of from about 300 to about 500 daltons. Also, one or more of the retentates obtained by embodiments of the filtration process of the present invention, which comprise the residue of the azole heteroaromatic compound-containing mixtures which does not (at least initially) pass through the membrane structure of these filtration membrane(s), may, in certain embodiments, be recycled or recirculated, partially or wholly, for further processing (e.g., may be again passed through these filtration membrane(s)), for example, by adding, partially or wholly, the retentate(s) back to the source of the feed flow which is passed through the filtration membranes.

In some embodiments of the present invention, a plurality of filtration units comprising one or more filtration membranes may be used through which the liquid feed flow of the azole heteroaromatic compound-containing mixture is passed to provide a plurality of permeates comprising the at least partially purified azole heteroaromatic compound-containing mixture(s), as well as a plurality of retentates comprising at least some residual impurities. In these embodiments, a first portion of the feed flow of the liquid azole heteroaromatic compound-containing mixture may be passed through an initial filtration section in step (b) to provide an initial permeate comprising an at least partially purified azole heteroaromatic compound-containing mixture and an initial retentate comprising at least some impurities. In certain embodiments, a second portion of the feed flow of step (a) may then be passed then be passed through an intermediate filtration section (positioned after the initial filtration section) having at least one or more intermediate filtration subsections (e.g., from one to thirteen subsections, such as from two to four subsections), to provide an intermediate permeate comprising an at least partially purified azole heteroaromatic compound-containing mixture, and an intermediate retentate comprising at least some impurities. In certain embodiments, a portion of the feed flow of step (a) may then be passed then be passed through a final filtration section (positioned after the intermediate filtration section) to provide a combined permeate comprising an at least partially purified azole heteroaromatic compound-containing mixture and a final retentate comprising at least some impurities.

In some embodiments involving filtration units/sections/subsections connected in sequence and in series, the retentate (wholly or partially) obtained from a filtration unit/section/subsection earlier in the sequence may be used to provide the feed flow for the next filtration unit/section/subsection in the sequence. In other embodiments, at least portion of the initial retentate, at least a portion of the intermediate retentate, and/or at least a portion of the final retentate (separately or combined) may be recycled or recirculated back, and added to the feed flow for further processing. In other embodiments, the intermediate filtration section may be omitted (with the final filtration section being positioned after the initial filtration section) with the initial retentate and the final retentate (separately or combined) being recycled or recirculated back, and added to the feed flow for further processing. In yet other embodiments, only the initial filtration section is used with all or a portion of the initial retentate being recycled or recirculated back, and added to the feed flow to the initial filtration section for further processing.

Figure 1:
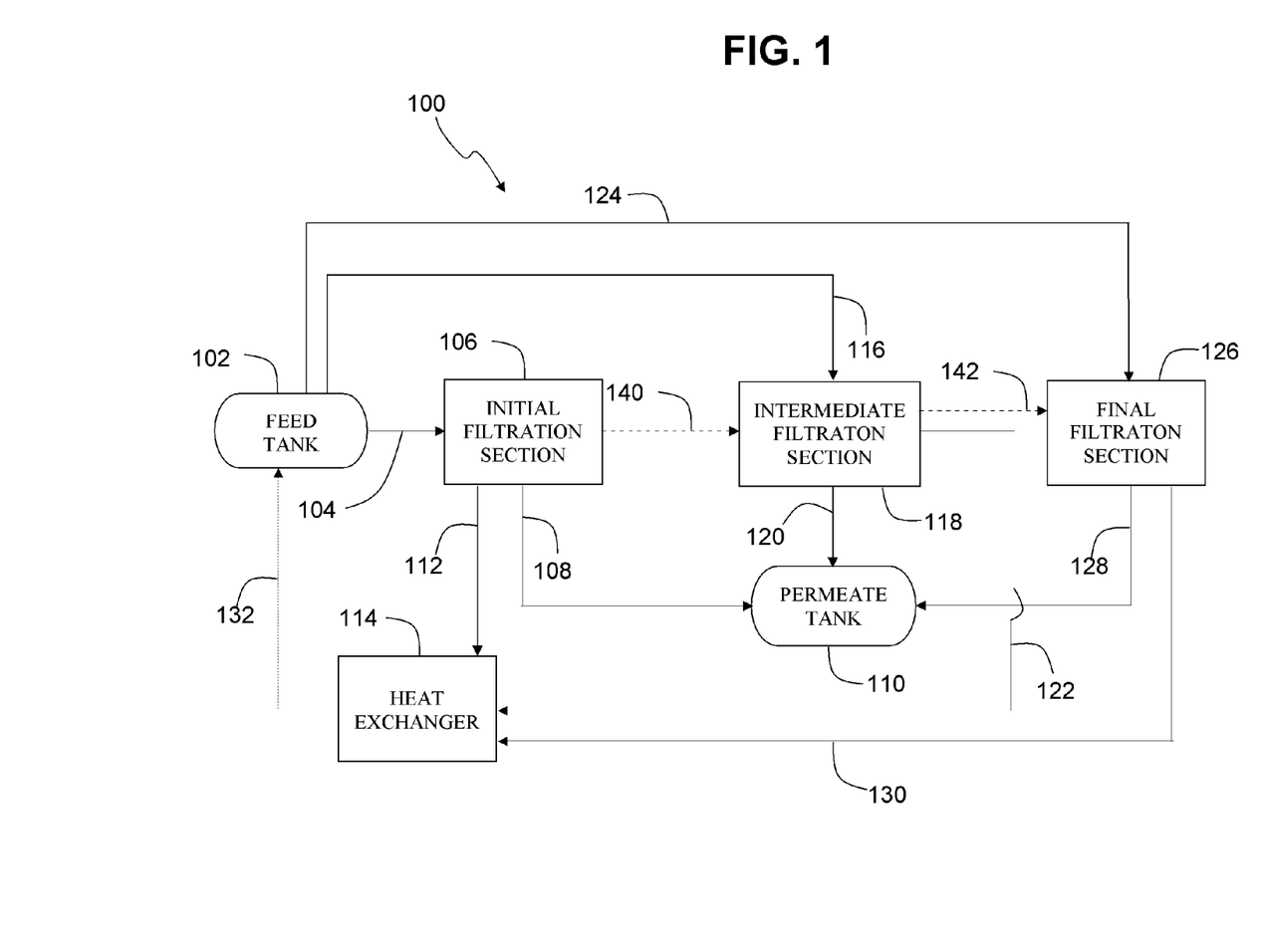
FIG. 1 represents a schematic diagram of an embodiment of the filtration process of the present invention using a filtration system comprising one to three filtration sections.

Embodiments of the filtration process of the present invention for providing purified concentrated triazoles are further illustrated in FIG. 1. FIG. 1 is a schematic diagram of a system for providing purified azole heteroaromatic compound mixtures (e.g., triazole-containing mixtures which will be referred to hereafter for illustrative purposes) according to an embodiment of the filtration process of the present invention, which is indicated generally as 100, and which is shown in this embodiment of system as having three filtration sections connected in series. In system 100, a (first) portion of the unpurified triazole containing-mixture comprising at least some impurities in a Feed Tank 102 is passed as a liquid feed flow, indicated by arrow 104, through a first Initial Filtration Section 106 of system 100. Feed flow 104 passes through Initial Filtration Section 106 which separates, by cross-flow filtration in the filtration unit(s) comprising Initial Filtration Section 106, feed flow 104 into a first (initial) permeate, indicated by arrow 108, comprising an at least partially purified triazole-containing mixture which may then be collected in Permeate Tank 110, and a first (initial) retentate, indicated by arrow 112, comprising at least some impurities. As shown in FIG. 1, in system 100, initial retentate 112 may then be passed through Heat Exchanger 114 which cools initial retentate 112 (for example, by passing cooler water over the heat exchanger coils).

As also shown in FIG. 1, in system 100, another (second) portion of the unpurified triazole containing-mixture comprising at least some impurities in a Feed Tank 102 is then passed as a liquid feed flow, indicated by arrow 116, through a second Intermediate Filtration Section 118 (which may comprise one or more intermediate filtration subsections) positioned after Initial Filtration Section 106. Similar to Initial Filtration Section 106, the filtration unit(s) of each intermediate filtration subsection comprising Intermediate Filtration Section 118 separates, by cross-flow filtration, intermediate feed flow 116 into a second (intermediate) permeate (which may comprise one or more one intermediate permeates if Intermediate Filtration Section 118 includes one or more intermediate filtration subsection) comprising an at least partially purified triazole-containing mixture, indicated by arrow 120, which is again collected in Permeate Tank 110, and a second (intermediate) retentate (which may comprise one or more one intermediate retentates if Intermediate Filtration Section 118 comprises one or more than intermediate filtration subsections), indicated by arrow 122, comprising least some impurities. Similar to initial retentate 112, intermediate retentate 122 may then be passed through Heat Exchanger 114 which then cools the intermediate retentate 122.

As further shown in FIG. 1, in system 100, another (third) portion of the unpurified triazole containing-mixture comprising at least some impurities in a Feed Tank 102 is then passed as a liquid feed flow, indicated by arrow 124, through a third Final Filtration Section 126 (which may comprise one or more filtration units). Similar to Initial Filtration Section 106 and Intermediate Filtration Section 118, each filtration unit of the Final Filtration Section 126 separates, by cross-flow filtration, final feed flow 126 into a third (final) permeate, indicated by arrow 128, also comprising an at least partially purified triazole-containing mixture which is again collected in Permeate Tank 110, and a third (final) retentate, indicated by arrow 130, also comprising at least some impurities. Similar to initial retentate 112 and intermediate retentate 122, final retentate 130 may then be passed through Heat Exchanger 114 which then cools the final retentate 128.

As also shown in FIG. 1 by dashed arrow 128, in system 100, all or a portion of the initial retentate 112, intermediate retentate 122, and final retentate 130 from Heat Exchanger 114 may be (wholly or partially) recycled/recirculated and added back, as indicated by dashed arrow 132, to Feed Tank 102 for further processing by system 100. System 100 may also omit Intermediate Filtration Section 118, and may also omit Final Filtration Section 126. In one embodiment of system 100, the filtration unit(s) of Initial Filtration Section 106, Intermediate Filtration Section 118 may each also comprise a spiral membrane structure, and Final Filtration Section 128 may each comprise a spiral membrane structure(s), a tubular membrane structure(s), or a combination of spiral and tubular membrane structure. In some embodiments of system 100, Initial Filtration Section 106, each subsection of Intermediate Filtration Section 114, and Final Filtration Section may each comprise two or more filtration units operating in parallel (e.g., a pair of filtration units operating in parallel).

In another alternate embodiment of system 100 also shown in FIG. 1 (i.e., where the filtration units of Initial Filtration Section 106, Intermediate Filtration Section 118, and Final Filtration Section 126 are connected in sequence and in series), the retentate (wholly or partially) obtained from Initial Filtration Section 106, and as indicated by dashed arrow 140, may be used to provide the feed flow for Intermediate Filtration Section 118. Again, the permeate 120 from Intermediate Filtration Section 118 may be collected in Permeate Tank 110. The retentate (wholly or partially) obtained from Intermediate Filtration Section 118, and as indicated by dashed arrow 142, may be used to provide the feed flow for Final Filtration Section 126. The final retentate 130 obtained from Final Filtration Section 126 may then be passed through Heat Exchanger 114, and as indicated by dashed arrow 132, may then be (wholly or partially) recycled/recirculated and added back to Feed Tank 102 for further processing by system 100.

Figure 2:
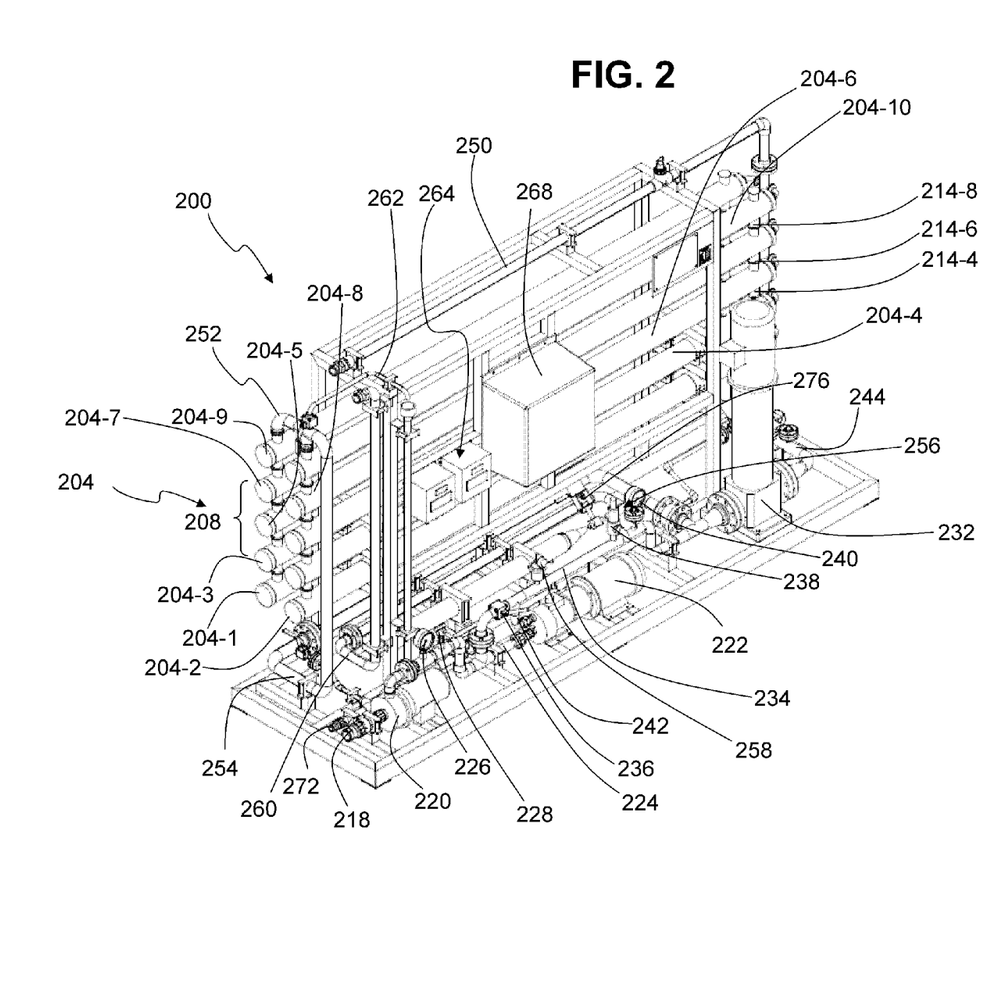
FIG. 2 represents a perspective view of an embodiment of a filtration system for carrying out the filtration process of the present invention comprising five vertically stacked filtration sections or subsections, and wherein each section or subsection comprises a pair of filtration units.
Figure 3:
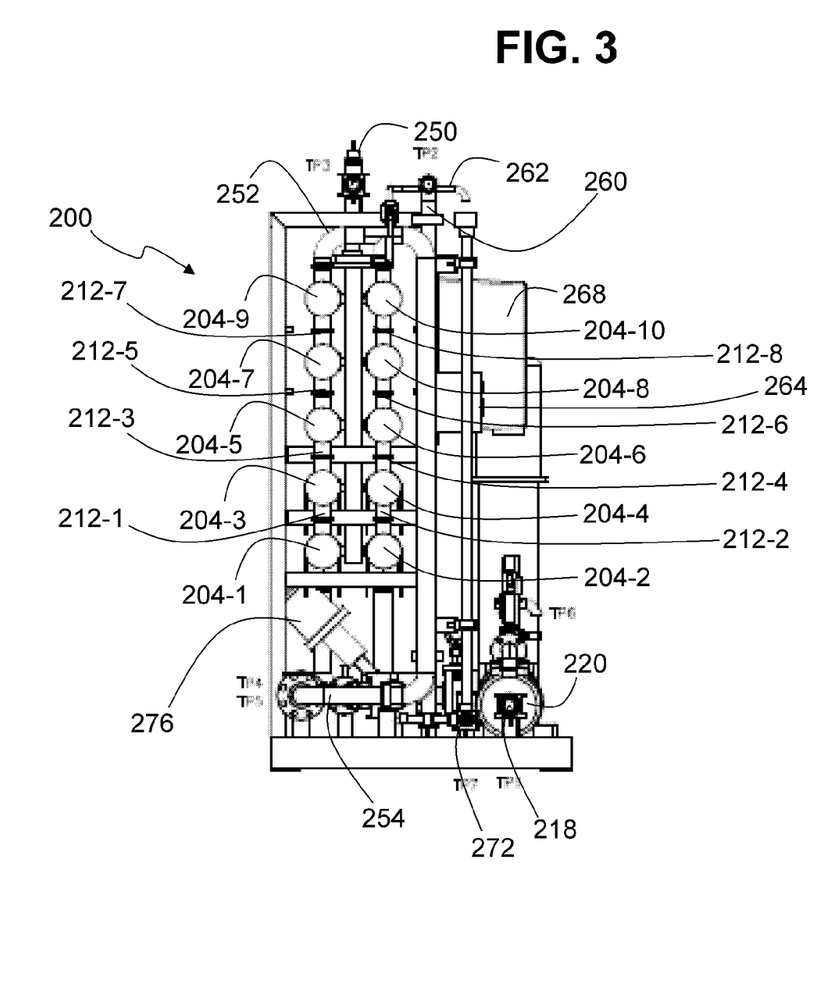
FIG. 3 represents a rearward end view of the embodiment of the filtration system of FIG. 2.

FIGS. 2 through 5 illustrate an embodiment of a filtration system for carrying the filtration process of the present invention which is indicated generally as system 200, and which is shown as comprising five filtration sections and/or subsections (corresponding to Initial Filtration Section 106, Intermediate Filtration Section 118, and Final Filtration Section 126 of FIG. 1) although system 200 may, in certain embodiments, also comprise as few as one filtration section (corresponding to Initial Filtration Section 106 or Final Filtration Section 120 of FIG. 1), two filtration sections (corresponding to Initial Filtration Section 106 and Final Filtration Section 126 of FIG. 1), or more than five filtration sections and/or subsections (i.e., including Intermediate Filtration Section 118 having more than three subsections). As shown in FIGS. 2 and 3, system 200 is shown as comprising ten filtration units indicated generally as 204 (i.e., filtration units 204-1 through 204-10) which are vertically stacked to provide sections and/or subsections, each section or subsection comprising a pair of filtration units (e.g., 204-1 and 204-2) operating in parallel. Each of the filtration units 204-1 through 204-10 comprise a pressure vessel which encloses, encompasses, surrounds, etc., one or more filtration membranes (e.g., from one to three filtration membranes connected in series), the particular number of membranes depending upon the length of the respective pressure vessel, as well as the length of the respective membrane(s). Each of filtration units 204-1 through 204-10 provides for cross-flow filtration with the feed flow comprising the liquid passing along the exterior surface of each filtration membrane such that the triazole-containing mixture in the feed flow passes inwardly through the wall of the filtration membrane to provide the purified triazole-containing mixture which collects as the permeate in the interior (hollow) core (for tubular membrane structures), or within the interior surface of the membrane (for spiral membrane structures). (In some embodiments involving tubular membranes, the feed flow may enter the interior core and then pass outwardly through the membrane such that the permeate collects, instead, along the exterior surface, while the residual retentate collects within the core.

The lowermost (bottom) pair of units 204-1 and 204-2 of system 200 correspond to the Initial Filtration Section 106. The three pairs of units 204-3/204-4, 204-5/204-6, and 204-7/204-8 positioned sequentially above units 204-1/204-2, and indicated generally by brace 208, of system 200 correspond to the respective subsections of Intermediate Filtration Section 118. The uppermost (top) pair of units 204-9 and 204-10 of system 200 correspond to the Final Filtration Section 126.

As shown in FIGS. 2 and 3, the rearward end of units 204 are connected by vertical extending retentate flow lines, indicated as 212-1 through 212-8 for permitting upward flow of retentate exiting from near the rearward end of units 204, starting with lower units 204-1 and 204-2 and ending with upper units 204-9 and 204-10. Specifically, vertical retentate flow line 212-1 connects unit 204-1 to adjacent unit 204-3, while vertical retentate flow line 212-2 connects unit 204-2 to adjacent unit 204-4; vertical retentate flow line 212-3 connects unit 204-3 to adjacent unit 204-5, while vertical retentate line 212-4 connects unit 204-4 to adjacent unit 204-6; vertical retentate flow line 212-5 connects unit 204-5 to adjacent unit 204-7, while vertical retentate line 212-6 connects unit 204-6 to adjacent 204-8; and vertical retentate flow line 212-7 connects unit 204-7 to adjacent unit 204-9, while vertical retentate line 212-8 connects unit 204-8 to adjacent unit 204-10. Similarly, and as shown in FIG. 2, the forward end of units 204 are also connected by vertical extending feed flow lines of which only three, indicated as 214-4, 214-6, and 218-8, are visible in FIG. 2 for permitting upward feed flow near the forward end of units 204, again starting with lower units 204-1 and 204-2 and ending with upper units 204-9 and 204-10. Units 204-1, 204-3, 204-5, 204-7, and 204-9 essentially operate as one column of connected filtration units, while units 204-2, 204-4, 204-6, 204-8, and 204-10 essentially operate as a second adjacent and parallel column of connected filtration units.

As further shown in FIGS. 2 through 5, system 200 further comprises a feed tank inlet port, indicated as 218, which provides the feed flow from Feed Tank 102 (not shown) to a booster pump, indicated as 220. System 200 further comprises a high pressure pump, indicated as 222, with a line, indicated as 224, connecting booster pump 220 to high pressure pump 222. Booster pump 220 may also be provided with a pressure gauge, indicated as 226, and a temperature gauge, indicated as 228 (which measures/shows the temperature of the feed flow). A recirculating pump, indicated as 232, is connected by a bypass line 234 from line 224, and is provided with a bypass valve, indicated by 236, which permits the feed flow to bypass high pressure pump 222, along with a pressure release valve, indicated as 238. A pressure gauge, indicated as 240, may be provided for high pressure pump 222. A line, indicated as 242, is also provided which connects pump 222 to line 234 after by pass valve 236 to permit the feed flow to enter recirculating pump 232 when bypass valve 236 is closed.

Figure 4:
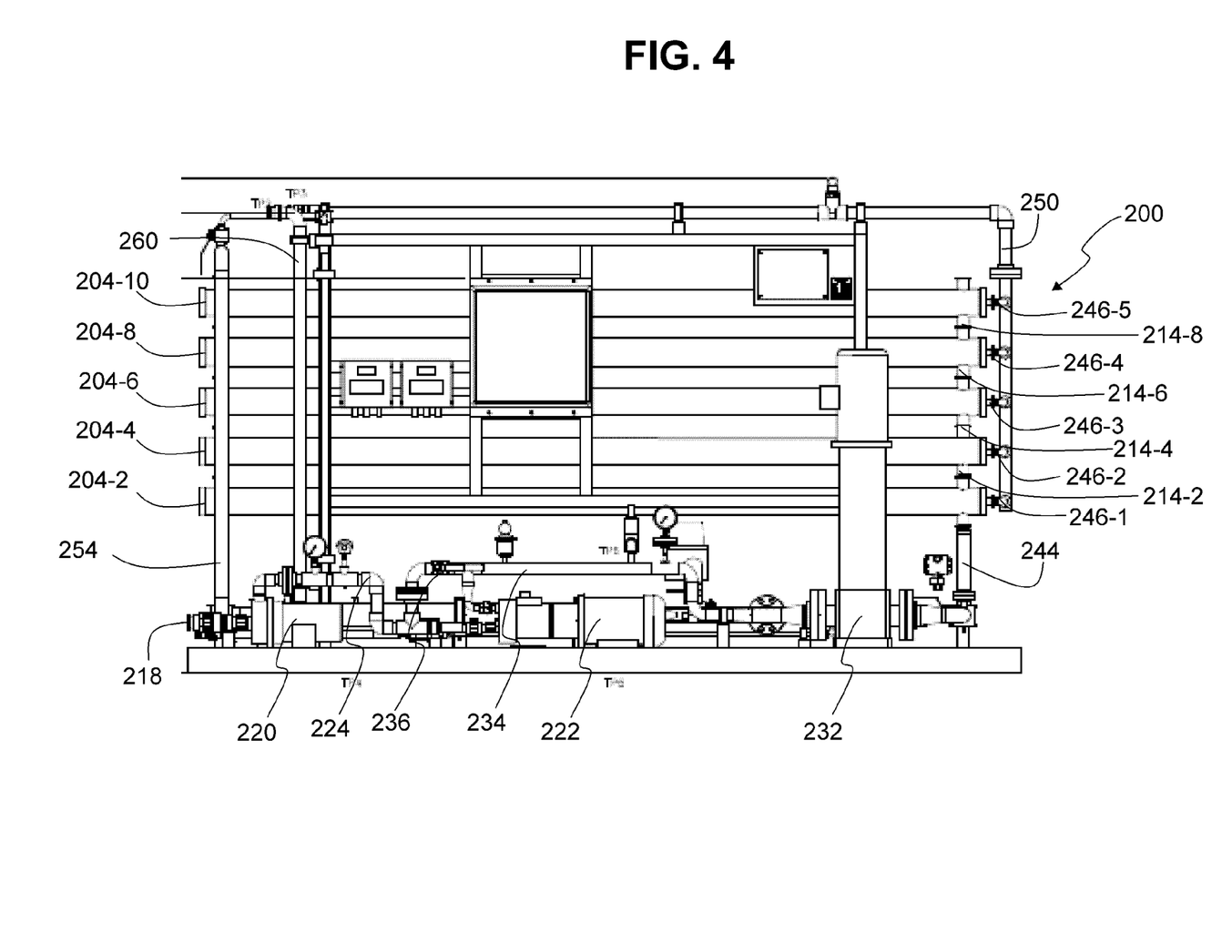
FIG. 4 represents a side view of the embodiment of the filtration system of FIG. 2.
Figure 5:
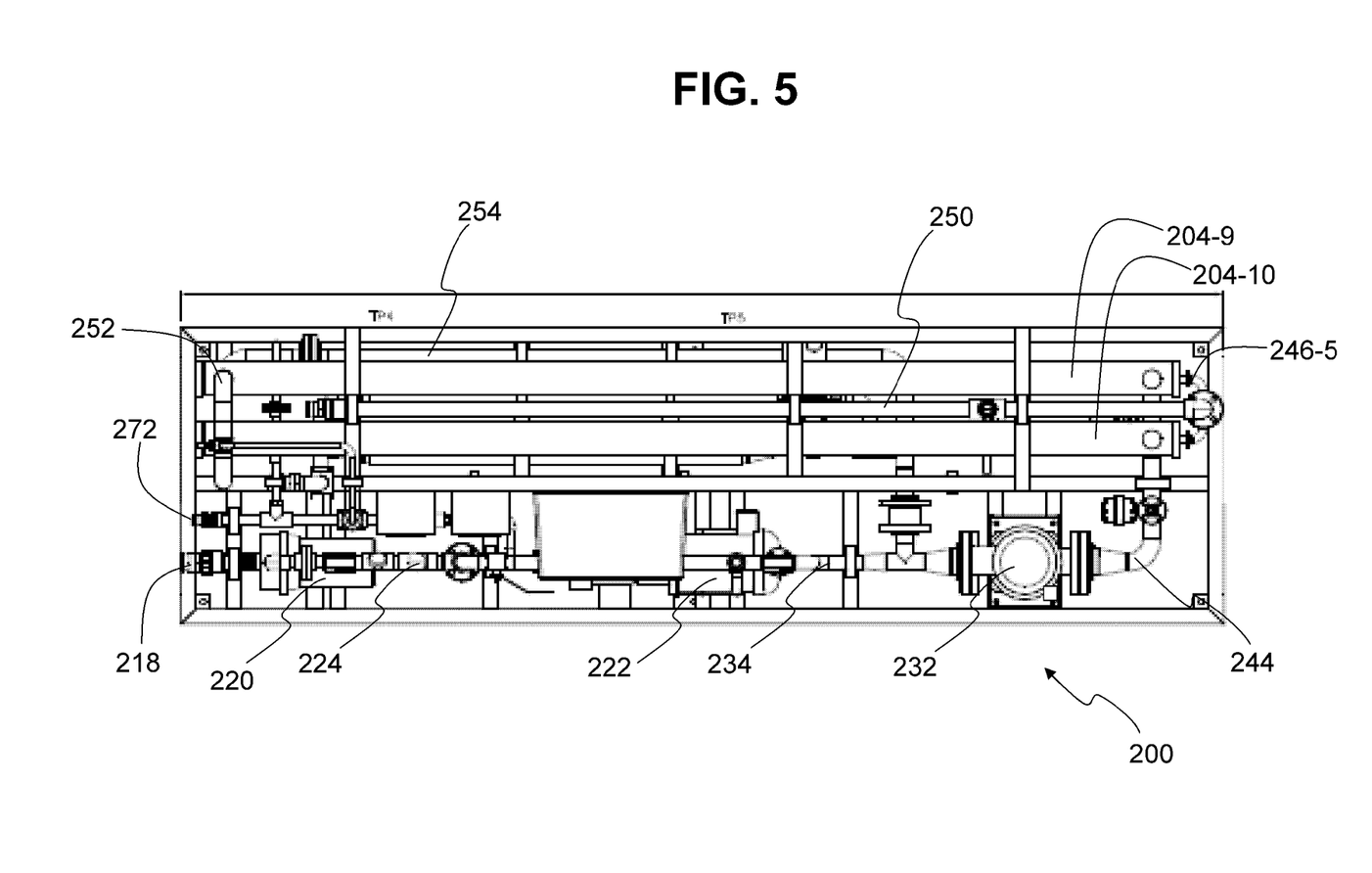
FIG. 5 represents a top plan view of the embodiment of the filtration system of FIG. 2.

As further shown in FIGS. 2, 4, and 5, a feed flow line, indicated as 244, connects recirculating pump 232 with the forward end of each of lower filtration units 204-1 and 204-2. As shown particularly in FIGS. 2 and 4, permeate exit lines, indicated as 246-1 through 246-5, are provided, and which connect the forward end of units 204 to main permeate line 250, with permeate exit line 246-1 connecting units 204-1 and 204-2, permeate line exit line 246-2 connecting units 204-3 and 204-4, permeate line exit line 246-3 connecting units 204-5 and 204-6, permeate line exit line 246-4 connecting units 204-7 and 204-8, and permeate line exit line 246-5 connecting units 204-9 and 204-10, respectively, to main permeate line 250. Also provided is a retentate exit port, indicated as 252, which connects units 204-9 and 204-10 to a main retentate line, indicated as 254. Main retentate line 254 is further connected to line 234 near recirculating pump 232. As indicated by arrow 256, a portion of main retentate line 254 splits off and is connected to a heat exchanger, indicated as 258. Heat exchanger 258 is also connected to a retentate exit line, indicated as 260, which is then connected to the Feed Tank 102 (not shown). System 200 is also provided with a retentate overflow drain, indicated generally as 262, which is connected to a drain line (not shown) and assists in bleeding air out from system 200 during start up and also permits retentate to drain out if there is a pressure build up in system 200, a pump power control box, indicated generally as 264, a main control box, indicated generally as 268, a drain valve, indicated as 272, which is connected at the end of the drain line (not shown), which opens the drain line to permit gravity draining of system 200, and a pressure regulator valve, indicated as 276, which regulates the pressure in the system 200. The opening (or closing) of valve 276 relieves or increases back pressure in system 200. The more valve 276 is closed, the more retentate flows back into system 200. Conversely, the more valve 276 is open, the more retentate flows through heat exchanger 258, thus leaving system 200.

In operation, the feed flow of the triazole-containing mixture from Feed Tank 102 enters system 200 through feed tank inlet port 218 due to the action of booster pump 220. This feed flow is further pulled into line 224 by booster pump 220 and into high pressure pump 222 to prime system 200. After system 200 is primed with feed flow from Feed Tank 102, bypass valve 236 is closed so that all of the feed flow then goes to high pressure pump 222. High pressure pump 222 then forces (pushes) the feed flow through line 234 and into recirculating pump 232. Feed flow from recirculating pump 232 then moves through feed flow line 244.

The feed flow from line 244 then enters the pair of initial units 204-1 and 204-2 near the forward end thereof, with a portion of the feed flow then traveling upwardly through vertical feed flow lines 214-1 (not shown) and 214-2 into adjacent units 204-3 and 204-4, also near the forward end thereof. A portion of the feed flow at the forward end of units 204-3 and 204-4 then continues to travel upwardly further through vertical feed flow lines 214-3 (not shown) and 214-4 into adjacent units 204-5 and 204-6, also near the forward end thereof. A portion of the feed flow at the forward end of units 204-5 and 204-6 then continues to travel upwardly further through vertical feed flow lines 214-5 (not shown) and 214-6 into adjacent units 204-7 and 204-8, also near the forward end thereof. A portion of the feed flow at the forward end of units 204-7 and 204-8 then continues to travel upwardly further through vertical feed flow lines 214-7 (not shown) and 214-8 into uppermost adjacent units 204-9 and 204-10, also near the forward end thereof.

A portion of the feed flow received from line 244 at the forward end of units 204-1 and 204-2 travels rearwardly over the exterior surface of the filtration membrane(s) in each of units 204-1 and 204-2. A fraction of the rearwardly traveling feed flow in units 204-1 and 204-2 passes through the porous membranes positioned within units 204-1/204-2 (i.e., those components in the feed flow having a molecular weight low/small enough to pass through the porous membranes), and collects within the interior (hollow) core thereof to provide an at least partially purified permeate which then exits through permeate exit port 246-1 and into main permeate line 250. The remaining portion of the feed flow traveling rearwardly in units 204-1 and 204-2 which does not pass through the porous membranes (i.e., those impurities in the feed flow having a molecular weight which is higher/larger so as not to pass through the porous membranes) then forms, respectively, a first retentate and second retentate which exits upwardly and respectively through retentate flow lines 212-1 and 212-2, and into the rearward end of adjacent units 204-3 and 204-4.

Similarly, a portion of the feed flow received at the forward end of units 204-3 and 204-4, respectively, from vertical feed flow lines 214-1 (not shown) and 214-2 travels rearwardly over the exterior surface of the filtration membrane(s) in each of units 204-3 and 204-4. A fraction of the rearwardly traveling feed flow in units 204-3 and 204-4 again passes through the porous membranes positioned within units 204-3/204-4 and collects within the interior (hollow) core thereof to provide an at least partially purified permeate which then exits through permeate exit port 246-2 and into main permeate line 250. The remaining portion of the feed flow traveling rearwardly in units 204-3 and 204-4 which does not pass through the porous membrane then forms, respectively a third retentate (with which the first retentate from unit 204-1 is also combined) and a fourth retentate (with which the second retentate from unit 204-2 is also combined) which exit, respectively upwardly through retentate flow lines 212-3 and 212-4, and into the rearward end of adjacent units 204-5 and 204-6.

Similarly, a portion of the feed flow received at the forward end of units 204-5 and 204-6, respectively, from vertical feed flow lines 214-3 (not shown) and 214-4 travels rearwardly over the exterior surface of the filtration membrane(s) in each of units 204-5 and 204-6. A fraction of the rearwardly traveling feed flow in units 204-5 and 204-6 again passes through the porous membranes positioned within units 204-5/204-6 and collects within the interior (hollow) core thereof to provide an at least partially purified permeate which then exits through permeate exit port 246-3 and into main permeate line 250. The remaining portion of the feed flow traveling rearwardly in units 204-5 and 204-6 which does not pass through the porous membrane then forms, respectively a fifth retentate (with which the combined first/third retentate from unit 204-3 is also combined) and a fourth retentate (with which the combined second/fourth retentate from unit 204-4 is also combined) which exit, respectively upwardly through retentate flow lines 212-3 and 212-4, and into the rearward end of adjacent units 204-5 and 204-6.

Similarly, a portion of the feed flow received at the forward end of units 204-7 and 204-8, respectively, from vertical feed flow lines 214-5 (not shown) and 214-6 travels rearwardly over the exterior surface of the filtration membrane(s) in each of units 204-7 and 204-8. A fraction of the rearwardly traveling feed flow in units 204-7 and 204-8 again passes through the porous membranes positioned within units 204-7/204-8 and collects within the interior (hollow) core thereof to provide an at least partially purified permeate which then exits through permeate exit port 246-4 and into main permeate line 250. The remaining portion of the feed flow traveling rearwardly in units 204-7 and 204-8 which does not pass through the porous membrane then forms, respectively a seventh retentate (with which the combined first/third/fifth retentate from unit 204-5 is also combined) and a eighth retentate (with which the combined second/fourth/sixth retentate from unit 204-6 is also combined) which exit, respectively upwardly through retentate flow lines 212-7 and 212-8, and into the rearward end of adjacent units 204-9 and 204-10.

Similarly, a portion of the feed flow received at the forward end of units 204-9 and 204-10, respectively, from vertical feed flow lines 214-7 (not shown) and 214-8 travels rearwardly over the exterior surface of the filtration membrane(s) in each of units 204-9 and 204-10. A fraction of the rearwardly traveling feed flow in units 204-9 and 204-10 again passes through the porous membranes positioned within units 204-9/204-10 and collects within the interior (hollow) core thereof to provide an at least partially purified permeate which then exits through permeate exit port 246-5 and into main permeate line 250. The remaining portion of the feed flow traveling rearwardly in units 204-9 and 204-10 which does not pass through the porous membrane then forms, respectively a final ninth retentate (with which the combined first/third/fifth/seventh retentate from unit 204-7 is also combined) and a tenth retentate (with which the combined second/fourth/sixth/eighth retentate from unit 204-8 is also combined).

The final ninth and tenth retentates from units 204-9/204-10 exit through retentate exit port 252 and then enter main retentate line 254 as a final combined retentate. A portion of the final combined retentate in main retentate line 254 passes through split 256 in main retentate line 254 and enters heat exchanger 258 to be cooled and then passed through retentate exit line 260 back to Feed Tank 102 (not shown). The remaining portion of the final combined retentate in main retentate line 254 is returned to line 234 and enters recirculating pump 232 to thus become part of the feed flow in feed flow line 244 that is passed initially to filtration units 204-1/204-2.

All documents, patents, journal articles and other materials cited in the present application are hereby incorporated by reference.

Although the present invention has been fully described in conjunction with several embodiments thereof, it is to be understood that various changes and modifications may be apparent to those skilled in the art. Such changes and modifications are to be understood as included within the scope of the present invention as defined by the appended claims, unless they depart therefrom.

What is claimed is:

1. A process for removing impurities from a liquid azole heteroaromatic compound-containing mixture, which comprises the following steps:
   (a) providing a liquid azole heteroaromatic compound-containing mixture comprising impurities; and having a PH of at least about 9; and
   (b) passing the azole heteroaromatic compound-containing mixture of step (a) in a cross-flow manner through at least one filtration membrane selected from the group consisting of nanofiltration and ultrafiltration membranes and having a molecular pore size in the range of from about 200 daltons to about 1 kilodalton to provide a permeate comprising an at least partially purified azole heteroaromatic compound-containing mixture and a retentate comprising at least some impurities.

2. The process of claim 1, wherein the at least one filtration membrane of step (b) has a molecular pore size in the range of from about 250 daltons to about 600 daltons.

3. The process of claim 2, wherein the at least one filtration membrane of step (b) has a molecular pore size in the range of from about 350 daltons to about 500 daltons and wherein the permeate of step (b) comprises components having a molecular weight below about 500 daltons.

4. The process of claim 3, wherein the permeate of step (b) comprises components having a molecular weight below about 300 daltons.

5. The process of claim 1, wherein step (b) is carried out by passing the azole heteroaromatic compound-containing mixture of step (a) through a plurality of filtration membranes.

6. The process of claim 5, wherein the plurality of filtration membranes comprise spiral membrane structures, tubular membrane structures, or a combination of spiral membrane structures and tubular membrane structures.

7. The process of claim 6, wherein each of the plurality of filtration membranes comprise spiral membrane structures.

8. The process of claim 5, wherein the plurality of filtration membranes comprise a plurality of filtration units connected in sequence and in series, and wherein at least part of the retentate obtained from a filtration unit earlier in the sequence is used to provide the feed flow for the filtration unit next in the sequence.

9. The process of claim 1, wherein the azole heteroaromatic compound-containing mixture of step (a) is passed through the at least one filtration membrane at pressure of from about 1 to about 2500 psi during step (b).

10. The process of claim 9, wherein the azole heteroaromatic compound-containing mixture of step (a) is passed through the through at least one filtration membrane at pressure of from about 100 to about 500 psi during step (b).

11. The process of claim 1, wherein the azole heteroaromatic compound-containing mixture of step (a) comprises at least about 5% of one or more triazoles.

12. The process of claim 11, wherein the azole heteroaromatic compound-containing mixture of step (a) comprises at least about 40% of one or more of benzotriazole, toluyltriazole, or a water-soluble salt thereof and has a pH in the range of from about 10 to about 14.

13. The process of claim 1, wherein the azole heteroaromatic compound-containing mixture of step (a) comprises up about 10% impurities.

14. The process of claim 13, wherein the azole heteroaromatic compound-containing mixture of step (a) comprises from about 0.1 to about 8% impurities.

15. The process of claim 1, wherein the azole heteroaromatic compound-containing mixture of step (a) comprises a liquid carrier comprising one more of: water, methanol, ethanol, propanol, isopropanol, ethylene glycol, propylene glycol, or diethylene glycol.

16. The process of claim 11, wherein the azole heteroaromatic compound-containing mixture of step (a) comprises at least about 50% of the one or more triazoles.

\* \* \* \* \*